United States Patent [19]

Volk

[11] Patent Number: 5,347,326
[45] Date of Patent: Sep. 13, 1994

[54] DIAGNOSTIC OR THERAPEUTIC CONTACT LENS

[76] Inventor: Donald A. Volk, 7893 Enterprise Dr., Mentor, Ohio 44060

[21] Appl. No.: 956,747

[22] Filed: Oct. 5, 1992

[51] Int. Cl.$^5$ .......................... A61B 3/00; G02C 7/01
[52] U.S. Cl. ............................... 351/160 R; 351/219
[58] Field of Search ................... 351/219, 160 R, 174, 351/247

[56] References Cited

U.S. PATENT DOCUMENTS

| | | | |
|---|---|---|---|
| Re. 29,229 | 5/1977 | Girard et al. | 351/160 |
| 2,653,515 | 9/1953 | Stimson | 88/54.5 |
| 2,989,894 | 6/1961 | Gordon | 88/54.5 |
| 3,212,097 | 10/1965 | Adler | 351/160 |
| 3,246,941 | 4/1966 | Moss | 315/160 |
| 3,431,046 | 3/1969 | Conrad et al. | 351/160 |
| 3,468,602 | 9/1969 | Rosen | 351/160 |
| 3,594,074 | 6/1971 | Rosen | 351/160 |
| 3,645,266 | 2/1972 | Morgan | 128/305 |
| 3,833,786 | 9/1974 | Brucker | 219/121 L |
| 4,068,933 | 1/1978 | Seiderman | 351/160 |
| 4,211,476 | 7/1980 | Brummel et al. | 351/160 R |
| 4,401,371 | 8/1983 | Neefe | 351/106 H |
| 4,561,737 | 12/1985 | Bourset et al. | 351/160 R |
| 4,571,040 | 2/1986 | Poler | 351/160 R |
| 4,621,912 | 11/1986 | Meyer | 351/160 R |
| 4,640,594 | 2/1987 | Berger | 351/160 R |
| 4,659,522 | 4/1987 | Neefe | 264/2.1 |
| 4,728,183 | 3/1988 | Heacock et al. | 351/219 |
| 5,007,729 | 4/1991 | Erickson et al. | 351/219 |
| 5,009,497 | 4/1991 | Cohen | 351/161 |
| 5,046,836 | 9/1991 | Volk | 351/219 |
| 5,189,450 | 2/1993 | Crossman et al. | 351/219 |
| 5,252,998 | 10/1993 | Reis et al. | 351/160 R |

FOREIGN PATENT DOCUMENTS 809894 3/1959 United Kingdom .......... 351/160

OTHER PUBLICATIONS

Spiro Vent Contact Lens Guide & Fitting Manual by Contact Lens Guild Inc. Rochester, N.Y. 1959.
Conforma Laboratories Advertisement in Optometric Weekly vol. 56 No. 43 Oct. 28, 1965 p. 15.

*Primary Examiner*—Loha Ben
*Assistant Examiner*—Michael A. Papalas
*Attorney, Agent, or Firm*—Oldham, Oldham & Wilson Co.

[57] ABSTRACT

There is disclosed a diagnostic or therapeutic contact lens for use in examination or treatment of the eye of a patient. The diagnostic or therapeutic contact lens comprises a lens body, constructed of a rigid, transparent material, and includes a concave posterior surface to be selectively positioned on the cornea of an eye. The posterior surface will preferably have a curvature substantially conforming to the curvature of the cornea and will be translationally movable on the cornea during observation or treatment to facilitate examination procedures. The posterior surface of the lens body may include channels for permitting the egress of air from between the posterior surface of the lens body and the surface of the cornea of the eye being examined. The channels may be located about the periphery of the optically functional portion of the posterior surface, such that air trapped in the precorneal region will be immediately displaced from the precorneal space so as to allow tear fluid of the eye to interface between the posterior surface and cornea. Subsequent to examination or treatment using the diagnostic or therapeutic contact lens, the channels for permitting the egress of air from the precorneal region will also facilitate removal of the lens from the cornea. The diagnostic or therapeutic contact lens will eliminate the need for using an ophthalmic solution in association therewith and will also substantially eliminate the creation of suction between the cornea and the contact lens.

20 Claims, 4 Drawing Sheets

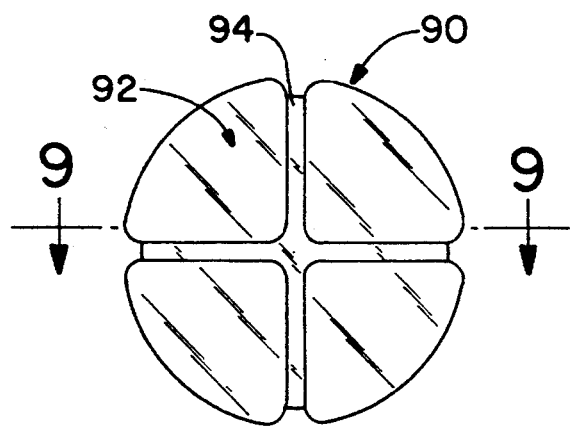
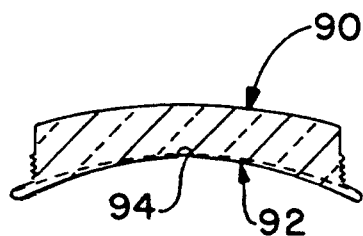
FIG.-8  FIG.-9
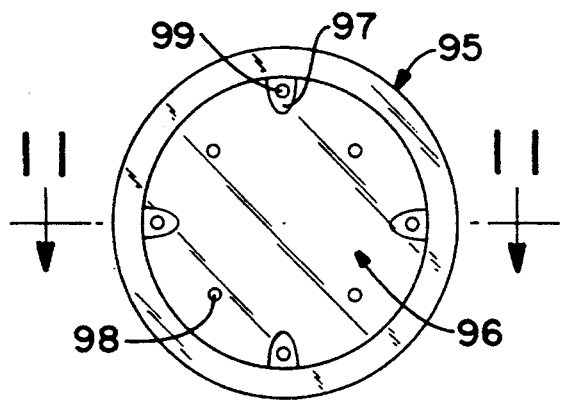
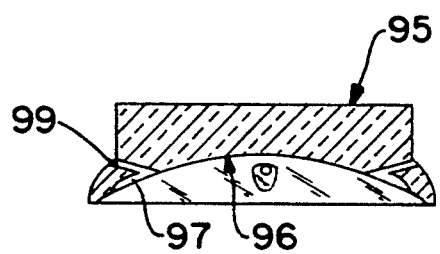
FIG.-10  FIG.-11
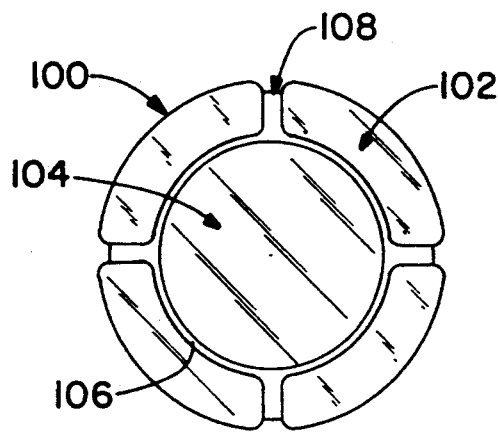
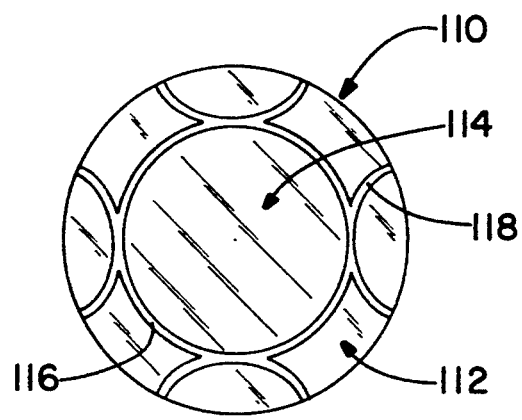
FIG.-12  FIG.-13

DIAGNOSTIC OR THERAPEUTIC CONTACT LENS

TECHNICAL FIELD

This invention relates generally to a contact lens utilized as or in a diagnostic or therapeutic ophthalmic instrument. The contact lens may be used to assist in observation of the eye in the diagnosis of eye disease, as an aid to surgical techniques and treatment, or for similar purposes. More specifically, the invention is directed to a contact lens for use in a diagnostic or therapeutic ophthalmic instrument which does not require the use of the interface solution conventionally utilized in association with such lenses, to thereby simplify and improve the diagnostic or therapeutic procedure.

BACKGROUND OF THE INVENTION

In the field of ophthalmology, there has been an increase in the use of contact lenses for ocular diagnosis and in various forms of ocular therapy. In this regard, a number of special contact lens instruments have been developed to assist the ophthalmologist or optometrist in the observation of the eye for diagnosis of eye disease, or in the performance of ocular surgical techniques and treatment. Such diagnostic or therapeutic contact lenses have significantly distinct characteristics that differentiate them from prescription contact lens which are used to correct refractive error of a patient's eye and thus achieve improved visual acuity.

In the use of a contact lens as an aid to vision, the front surface of the lens will act as a substitute for the anterior surface of the cornea, such that the lens may correct the irregularities of the front surface of the cornea which would not be correctable using conventional spectacles. In addition, the principle type of contact lens in current use corrects the usual refractive errors which also would be correctable with spectacles. In the development of contact lenses as an aid to a patients vision, emphasis has been placed upon eye health as well as the comfort with which such lenses can be worn. For example, until the latter part of the 1940's, almost all contact lenses utilized to aid vision had a portion resting directly on, or arching over, the cornea, with a supporting flange resting beyond the limbus on the sclera of the eye. Such lenses were referred to as scleral lenses, and were normally constructed of a glass material.

Subsequently, the feasibility of using plastic for lens fabrication was demonstrated with the introduction of a methyl methacrylate plastic molded scleral contact lens. The use of plastics led to the "hard" plastic corneal contact lens, which provided a lens of smaller diameter positioned within the limbal area of the cornea. These plastic materials, such as poly-methyl methacrylate (PMMA) had hydrophobic properties which reduced safe wearing time and may have caused discomfort to the wearer. The desired aspect of comfort, extended wearing times and eye health led to further developments, such as the development of soft "hydrophilic" gel lenses synthesized by copolymerization of hydroxyethylmethacrylate (HEMA) with ethylene glycol diamethacrylate (EGDM). Lenses constructed of such materials had hydrophilic properties with increased permeability to water, oxygen and low molecular weight constituents of tears, thereby providing metabolic advantages. Most recently, new lens materials have been introduced which are highly gas-permeable, and without any appreciable water content, such that extended wearing times can be achieved along with other various advantages.

In the use of contact lenses as an aid to a patient's vision, eye health has been and remains of major concern. Particularly, there is a need to supply oxygen to the corneal epithelium. This has been problematic with some of the materials utilized for fabricating corrective contact lenses. The corneal epithelium requires about eight percent (8%) oxygen for a proper aerobic glucose metabolism. The oxygen is supplied by the precorneal tear film naturally occurring in the eye. When wearing a corrective contact lens, the lens must either allow transmission of oxygen through the lens or must fit such that tear film exchange occurs beneath the lens. At the time of the blinking movement of the eye, tear exchange occurs by a pumping of tears from the tear reservoir. The corrective contact lens may facilitate this pumping action by means of lens movement during blinking. For proper eye health, the lid pumping action associated with corrective contact lenses may be necessary to prevent corneal anoxia.

With prescription contact lenses adapted to correct refractive error of an eye, various developments have been implemented to facilitate tear exchange or proper oxygen transmission to the cornea so as to maintain corneal health. Such designs include the rigid gas permeable contact lenses which allow transmission of gases through the lens to facilitate exchange of oxygen and carbon dioxide. One prescription contact lens design included a spiral vent lens having a design which theoretically provided a "jet propulsion" type of effect, wherein depressions in the concave surface of the lens were provided to produce rotation of the lens on the eye cornea so as to prevent tear fluid stagnation under the lens. Other corrective contact lens designs also provided means to promote tear exchange beneath the lens, which include the use of recesses, fenestrations or other various mechanical features to allow transmission of tear fluid into and out of the region beneath the contact lens. In each of these designs, tear exchange beneath the lens was of prime consideration so as to maintain eye corneal health while also allowing a more comfortable fit to facilitate the wearing of such lenses for longer periods of time. Many of these contact lens designs also relied upon the lid pumping action to accomplish the desired tear exchange.

Each of the above types of prescription contact lenses was conventionally designed to have a minimum thickness to also aid in comfortable wearing of the lenses. Such lenses, as well as many prescription contact lenses manufactured today, are typically between 0.10–0.30 mm, and allow the lid of the eye to close thereover. The minimum thickness of these lenses facilitates the desired pumping action and tear exchange beneath the lens.

As a completely distinct application from corrective lenses, contact lenses have also been used as an aid in diagnostic and surgical or laser treatment applications. A number of special contact lenses have thus been developed to assist eye care professionals in diagnosing and/or treating eye disease. Such diagnostic and therapeutic contact lenses may be used for corneal observation and for diagnosis of corneal abnormalities. Other diagnostic or therapeutic contact lenses include gonioscopy lenses which are designed for observation of the angle of the anterior chamber of the eye. Certain gonioscopy contact lenses are adapted to partially or completely neutralize the power of the cornea so as to enable observation of the anterior chamber angle directly or by means of mirrors. Gonioscopy lenses are generally utilized in conjunction with a slit lamp biomicroscope or other microscope, wherein light from a slit lamp is reflected into the anterior chamber angle, and returns along the same path to be viewed through the microscope.

Alternatively, diagnostic or therapeutic contact lenses may be used in observation of the ocular fundus when employed with a slit lamp biomicroscope or other microscope. Special contact lens have been developed for use in a technique known as direct ophthalmoscopy, wherein an erect virtual image of the retina is produced. Another diagnostic procedure, indirect ophthalmoscopy, may also utilize a contact lens system to form a real, inverted image of the fundus, which may then be viewed with a slit lamp biomicroscope or other microscope.

Diagnostic or therapeutic contact lenses have also been utilized in laser surgery, such as photocoagulation treatment, and particularly in iridectomy, trabeculotomy, capsulotomy, vitrectomy, and other treatment procedures. With the use of lasers in eye treatment, attention has been given to avoid the risk of damage by the laser beam to areas of the eye which are not intended to be treated. A contact lens may be utilized to minimize the amount of energy to those portions of the eye which are not to be treated. Anti-reflection coatings may be used on these optical lenses, which facilitate transmission of laser energy to the proper areas of the eye. Diagnostic or therapeutic lenses have been utilized to image the eye structure which is to be treated, so as to enable accurate location of the laser beam focus. Contact lenses may also be utilized to increase the cone angle of the laser beam so as to dissipate the energy of the laser beam both in front and beyond its focus so as to avoid damage to eye tissue adjacent the areas to be treated. These and other special contact lenses may therefore be used both to facilitate surgical techniques as well as to protect those portions of the eye from energy introduced by the laser beam.

In the use of such diagnostic or therapeutic contact lenses, an ophthalmic solution is conventionally utilized to fill any precorneal space between the diagnostic or therapeutic contact lens and the cornea of the eye being examined. The use of an artificial fluid may additionally aid in the prevention of oedema, which can interfere with observation and diagnosis. The ophthalmic solution may further facilitate translational movement of the diagnostic or therapeutic contact lens on the cornea for observation of different areas of the eye being examined. The ophthalmic solution also acts in conjunction with the diagnostic or therapeutic contact lens to essentially neutralize any corneal irregularities thus facilitating ophthalmoscopic or slit lamp examination of the eye. The diagnostic or therapeutic contact lens, in association with the ophthalmic solution, will essentially eliminate the refractive power of the cornea from the optical system.

Unfortunately, the use of ophthalmic solution in association with a diagnostic or therapeutic lens has been found to have many disadvantages. These disadvantages make use of diagnostic or therapeutic contact lenses by a practitioner difficult, or make the diagnostic or treatment procedures objectionable to a patient. The use of an ophthalmic solution in association with a diagnostic or therapeutic contact lens firstly creates the additional step of solution application which the practitioner must perform prior to diagnosis or treatment utilizing the lens instrument. The use of an ophthalmic solution adds another step in the diagnostic or therapeutic procedure and creates an additional expense to the practitioner. Additionally, residual ophthalmic solution from the diagnostic or therapeutic procedure may also remain and dry on the diagnostic or therapeutic contact lens, as well as the eyelids of the patient. This will again add to the steps which must be performed in the diagnostic procedure, in the removal of residual fluid after examination. Similarly, the patient's vision may be blurred after examination or treatment, as the ophthalmic solution remains on the eye and may require flushing or other cleaning procedures to clear and restore the patient's vision or to allow subsequent ocular photography.

Other problems associated with the use of an ophthalmic solution with a diagnostic or therapeutic contact lens include the possibility of producing corneal epithelial changes, which can result if the ophthalmic solution is not properly chemically balanced with respect to Ph and/or tonicity. These corneal epithelial changes may inhibit proper examination or observation of eye structures, and may further inhibit follow up diagnosis and/or treatment after initial examination. For example, fundus photography may not be possible as a result of epithelial changes caused by the use of the ophthalmic solution. Follow-up diagnosis or treatment procedures using contact or non-contact lens methods are many times desired to be performed by a practitioner subsequent to initial examination. With the use of an ophthalmic solution, follow up diagnosis or treatment may be more difficult, or may be impossible if using non-contact methods.

Another disadvantage of using an ophthalmic solution in association with a diagnostic or therapeutic contact lens is found in that air may be entrapped within the gel or solution in the precorneal space between the contact lens and the cornea of the eye being examined. These bubbles will inhibit proper examination or treatment using the contact lens. The formation of bubbles under the contact lens is a significant disadvantage of contact diagnostic and treatment procedures, and is created as a result of the use of an ophthalmic solution in the precorneal space between the contact lens and the cornea and/or the contact lens design. The formation of bubbles between the contact lens and the cornea will result in image distortion or blurring, as well as possible distortion of laser beam transmission through the lens.

Other problems associated with the use of an ophthalmic solution in association with a diagnostic or therapeutic contact lens are found in that the patient being examined must be positioned in an orientation such that the ophthalmic solution will remain in the precorneal space between the contact lens and cornea. Difficulty may be encountered if the patient's head is not in a vertical position, wherein upon the attempted application of the lens on the eye the ophthalmic solution may run out from the precorneal space and bubbles may form. Subsequent to diagnosis or treatment, the ophthalmic solution also is found to contribute to the suction of the lens on the cornea of the eye being examined, making the lens difficult to remove and causing discomfort to the patient.

SUMMARY OF THE INVENTION

Based upon the foregoing, there has been found to be a need for a diagnostic and therapeutic contact lens which will avoid many of the difficulties or objectionable characteristics associated with diagnosis or treatment utilizing contact methods. It is therefore a main object of the invention to provide a diagnostic or therapeutic contact lens which will eliminate the need to use an ophthalmic solution in association with the diagnostic or therapeutic contact lens.

Another object of the invention is to provide a diagnostic or therapeutic contact lens allowing simplified examination or treatment of the patient's eye, after which the patient's vision will remain as clear and unobstructed as it was prior to the application of the lens.

It is another object of the invention to provide a diagnostic or therapeutic contact lens which facilitates follow up diagnosis and/or treatment after examination or observation using the contact lens.

Another object of the invention to provide a diagnostic or therapeutic contact lens which includes means by which air may be immediately displaced from the precorneal space between the cornea and diagnostic or therapeutic contact lens, to eliminate the possibility of image distortion or blurring, as well as distortion of a laser beam or the like caused by bubbles formed under a lens.

Another object of the invention is to provide a diagnostic or therapeutic contact lens wherein minimal suction will be created between the posterior surface of the lens and the cornea of the eye being examined, such that the contact lens may be easily removed from the cornea subsequent to examination.

Yet another object of the invention is to provide a diagnostic or therapeutic contact lens wherein the use of an ophthalmic solution in association therewith is eliminated, such that the cornea will remain clear and without epithelial changes which may occur due to the use of an ophthalmic solution.

Still another object of the invention to provide a diagnostic or therapeutic contact lens which allows examination or treatment of the eye to be accomplished in any patient orientation, and eliminates the additional steps of solution application and cleanup in the diagnostic, therapeutic and/or treatment procedures.

These and other objects of the invention are accomplished by means of a diagnostic contact lens instrument for use in examination or treatment of the eye of a patient, which comprises a lens body, constructed of a rigid transparent material, and includes a concave posterior surface to be selectively positioned on the cornea of an eye. The posterior surface preferably has an aspheric shape substantially conforming to that of the cornea at least over an optically functional portion thereof, and will be movable on the cornea during observation or treatment to facilitate examination and treatment procedures. The lens body may include means for permitting the egress of air from between its posterior surface and the surface of the cornea of the eye being examined. The means to permit the egress of air from the precorneal space may be located about the periphery of the posterior surface of the contact lens, and may be formed as channels, openings or other similar means. The channels or other means function in a manner such that air entrapped within the region about the optically functional portion of the posterior surface of the contact lens will be substantially immediately displaced and issued out from within the precorneal space. This allows the tear fluid of the eye to interface between the posterior surface of the contact lens and the corneal surface in the central or optically functional region. Subsequent to examination or treatment using the diagnostic or therapeutic contact lens, the means for permitting the egress of air from the region about the optically functional portion of the posterior surface will also facilitate removal of the lens from the cornea by minimizing or eliminating suction between the cornea and the contact lens.

In a first embodiment, the diagnostic or therapeutic contact lens of the invention may have a posterior surface with a diameter being smaller than the cornea of the eye, such that the posterior surface may be positioned on the corneal surface without contacting the limbal area or scleral portion of the eye. A posterior surface having such a diameter may be positioned on the cornea and can be translationally moved for examination or treatment. The shape of the posterior surface may be aspheric with a peripheral slope less than that of the average cornea. This shape along with the lens diameter will minimize the creation of air bubbles in the precorneal region along with suction between the lens and the cornea.

In another preferred embodiment, the diagnostic or therapeutic contact lens of the invention includes means for permitting the egress of air from the precorneal region about the center of the posterior surface of the lens body. The means for permitting the egress of air may be channels formed in portions of the posterior surface, which provide a means of displacement of any air from between the cornea and contact lens about the optically functional region of the posterior surface. The channels to permit the egress of air from the region between the posterior surface of the lens and the cornea may have varying depth and/or width. The design of the channels will create a space having increased volume toward the periphery of the lens, which will facilitate drawing any trapped air from the precorneal space outwardly from the optically functional region of the lens. As the diagnostic or therapeutic contact lens body has significant thickness, relative to prescription contact lens, the channels formed in the posterior surface of the lens body are desired to have a substantial depth which will facilitate transmission of air from the center portion of lens. The channels may preferably have a depth of at least 0.15 in. at its maximum depth, but may have a greater depth if desired and may be shaped to have an increasing depth and/or width toward the peripheral region of the lens body. Various numbers of channels may be utilized to allow the egress of air from the precorneal region, but a uniform distribution of channels on the posterior surface has been found to provide the desired attributes mentioned previously. The channels formed in the posterior surface are preferably positioned so as not to interfere with or inhibit observation of eye structures during examination or treatment procedures. For example, with indirect ophthalmoscopy of the fundus of the eye, the channels formed in the posterior surface of the contact lens will not extend into the center or optically functional region of the lens, through which light rays emanating from the fundus of the eye pass in the formation of a fundus image. Alternatively, in a gonioscopy lens, the channels may be located in peripheral portions of the posterior surface which are not utilized in observation of the angle of the anterior chamber. Alternative arrangements for the channels to permit the egress of air from the precorneal space, may be utilized for any particular diagnostic or treatment procedure for which the diagnostic or therapeutic contact lens is to be used.

Alternatively, apertures or holes may be provided in regions of the posterior surface of the diagnostic or therapeutic contact lens to allow air which may be trapped in the precorneal space to be immediately displaced. Such holes may be used in conjunction with channels formed in the posterior surface of the lens body to facilitate displacement and egress of air from the precorneal space. In another embodiment, a channel may be formed across the entire posterior surface of the diagnostic or therapeutic contact lens body. In this embodiment, the material from which the lens body is constructed may be a transparent solid material characterized by having an index of refraction approximating that of human tears so as to minimize any aberrations due to light refraction through the channel portion of the posterior lens surface. Also, apertures may be provided to extend from the exterior of the lens body to the formed channels on the posterior surface, to facilitate the egress of air from the precorneal space.

In another embodiment, the diagnostic therapeutic contact lens may include channels similar to the embodiment previously described in that they will permit the egress of air from the region between the lens and the cornea. In this embodiment, the optically functional portion of the posterior surface of the contact lens may be circumferentially inscribed with a channel which will act to draw any trapped air from the precorneal space outwardly from the optically functional area. The circumferentially inscribed channel may then be connected to a further channel which allows escape of any air bubbles in the desired manner. Alternatively, the grooves may be formed in a manner wherein a portion of a groove will extend to a position adjacent the optically functional area of the posterior surface, and a plurality of such channels may be formed to surround the optically functional area of the posterior surface and allow the egress of any trapped air bubbles from the precorneal space. Similar to the previous embodiments, the channels or similar means may also be coupled to a hole formed from the posterior surface to the exterior of the lens if desired. Further, as with the other embodiments, the means to allow egress of air from the precorneal space will substantially eliminate or minimize suction between the posterior surface of the lens and the cornea upon attempted removal of the lens from the cornea.

BRIEF DESCRIPTION OF DRAWINGS

These and other aspects and advantages of the invention will become apparent upon a further reading of the detailed description of the invention in conjunction with the drawings, wherein:

FIG. 8 is a plan view of the posterior surface of an alternate embodiment of the diagnostic or therapeutic contact lens of the invention;

FIG. 9 is a vertical cross-sectional view of the embodiment of a diagnostic or therapeutic contact lens, taken along line 9—9 shown in FIG. 8;

FIG. 10 shows a plan view of the posterior surface of an alternate embodiment of the diagnostic or therapeutic contact lens of the invention;

FIG. 11 shows an enlarged vertical cross-sectional view of the lens as shown in FIG. 10, as may be taken along line 11—11 thereof;

FIG. 12 shows a plan view of the posterior surface of an alternate embodiment of the diagnostic or therapeutic contact lens of the invention;

FIG. 13 shows a plan view of the posterior surface of an alternate embodiment of the diagnostic or therapeutic contact lens of the invention;

DETAILED DESCRIPTION OF THE INVENTION

Figure 1:
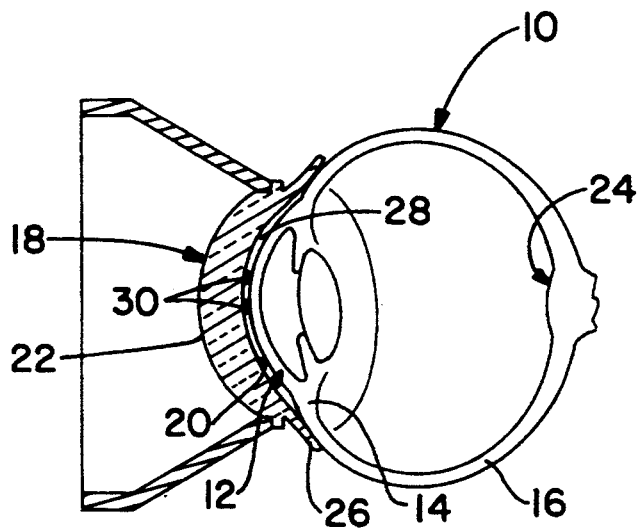
FIG. 1 is a vertical cross-section of a human eye to which there has been applied a diagnostic or therapeutic contact lens conventionally used in the prior art.

Turning now to FIG. 1, there is shown a human eye 10 having a cornea 12, and with a limbal region 14 and sclera 16 associated therewith. A contact lens 18 includes a posterior surface 20 and an anterior surface 22, and is conventionally fabricated from a non-absorbent, non-toxic, rigid, transparent material, such as a number of commercially available plastic materials including polymethyl methacrylate, polyethylene/polypropylene, polyethylene/polyvinylacetate copolymer compounds or the like. The posterior surface 20 of contact lens 18 will be a concave surface shaped to be applied to the cornea 12 of eye 10 for diagnosis or treatment. The posterior surface will conventionally be contoured so as to vault a portion of the cornea, with the ophthalmic solution conventionally used with diagnostic contact lenses filling the space between the cornea and posterior surface. The contact lens 18 as shown in FIG. 1 may be associated with a device for viewing the fundus 24 of eye 10 or alternatively may be associated with a gonioscopy device for viewing the anterior chamber angle of the eye 10. Each of these diagnostic or therapeutic instruments, as well as the wide variety of others, may utilize an anterior surface 22 having a different configuration, or be associated with additional lenses, mirrors, or the like. For example, gonioscopy contact lenses at times include internally reflecting or mirrored surfaces to allow observation of the anterior chamber angle. The posterior surface 20 of contact lens 18 also includes a scleral portion 26 which facilitates stabilization and positioning on the cornea 12.

In use of a diagnostic or therapeutic contact lens 18, an ophthalmic solution, such as methyl cellulose, is applied to the contact lens 18 and thereafter the lens is applied to the cornea 12 of eye 10 to create a fluid layer and interface 28 between posterior surface 20 of contact lens 18 and the cornea 12. As mentioned previously, in the use of an ophthalmic solution with the diagnostic or therapeutic lens 18, a common problem occurs in that bubbles 30 are formed in the precorneal space between posterior surface 20 of contact lens 18 and cornea 12. The other disadvantages of the use of an ophthalmic solution in association with the diagnostic or therapeutic contact lens 18 have been mentioned previously, and occur in the use of many conventional diagnostic or therapeutic contact lenses.

Figure 2:
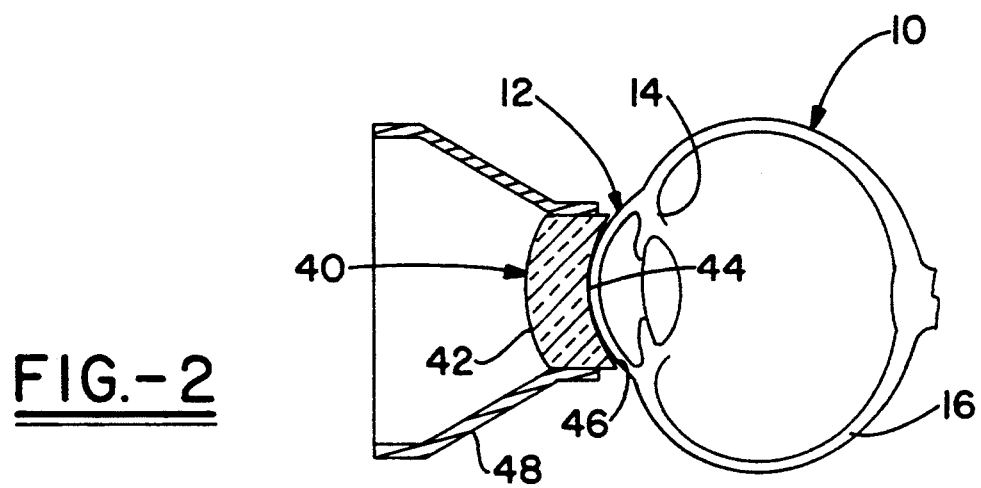
FIG. 2 is a vertical cross-sectional view of a human eye having applied thereto a first embodiment of a diagnostic or therapeutic contact lens in accordance with the invention.
Figure 3:
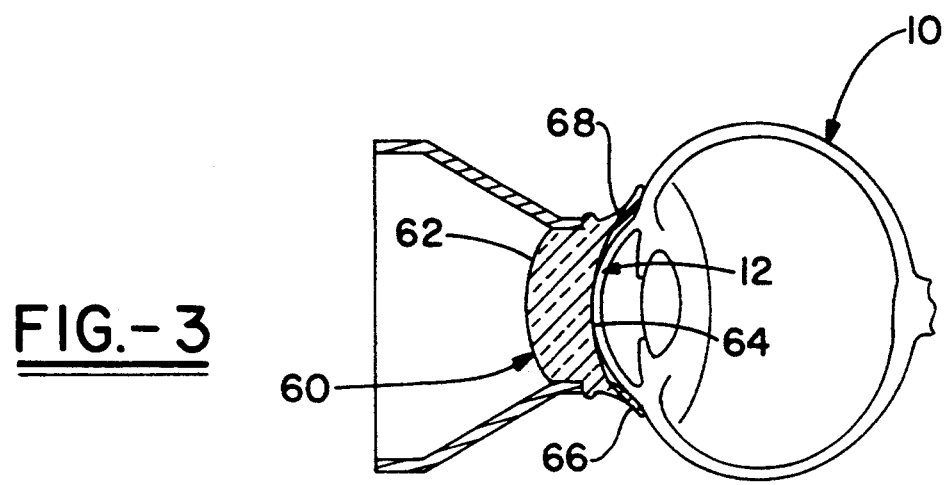
FIG. 3 is a vertical cross-sectional view of a human eye having applied thereto another preferred embodiment of diagnostic or therapeutic contact lens in accordance with the invention.

In FIG. 2, the diagnostic or therapeutic contact lens 40, representing a first embodiment of the invention, is positioned on cornea 12 of a patient's eye 10. The diagnostic or therapeutic contact lens 40 includes an anterior surface 42, which may be of any desired surface configuration for the particular diagnostic or therapeutic procedure to be performed. The anterior surface 42 may be of positive or negative in curvature and may be spherical or aspherical in its surface contour. The anterior surface 42 may additionally be planar or have associated therewith additional lens elements, mirror devices, or the like. The diagnostic or therapeutic contact lens 40 also includes a concave posterior surface 44, which in the preferred embodiment has a surface contour which substantially conforms to the shape of cornea 12. As has been recognized, the surface contour of cornea 12 for the human eye 10 is of aspherical configuration, and in the preferred embodiment, the posterior surface 44 will have an aspherical surface corresponding to the aspherical contour of the cornea. The posterior surface curvature of the diagnostic or therapeutic contact lens 40 may be defined by the polynomial:

$$Y = (2rx + (e^2 - 1)x^2)^{\frac{1}{2}} + Ax^F + Bx^G + Cx^H$$

where, the values of r, e, A, B, C, F, G, and H are chosen to accomplish the desired corneal fit, and having a peripheral slope less than that of the average cornea at an equivalent diameter. As an example, for the posterior surface 44, the apical radius of curvature, r, may range from 7.0 to 8.5 and e, representing apical eccentricity, may range from 0.0 to 1.2. Coefficients A, B, and C may range from $-10$ to 10 with exponents F, G, and H ranging from 0.5 to 10. The posterior surface 44 is flattened at the peripheral regions of surface 44 be flattened as indicated at 46. As mentioned previously, the diagnostic or therapeutic contact lens 40 of the invention is to be utilized for diagnosis or treatment of eye disease without the use of an ophthalmic solution as in prior practice. By conforming the posterior surface 44 to closely approximate the surface contour of an average cornea 12, any air located between the posterior surface 44 and the cornea 12 upon application of the lens 42 will be immediately displaced toward the periphery of the lens, thus avoiding image distortion, blurring or other undesired characteristics. This action is facilitated by reducing the diameter of the lens and progressively flattening the peripheral regions of lens 40 at 46, to a slope which is less than that of an average cornea at an equivalent diameter. Air will be more easily displaced from the interface region between the lens and cornea upon application of the lens. The flattened peripheral regions 46 of the posterior surface 44 as well as the reduced diameter of the lens 40 further facilitate translational movement of contact lens 40 on the cornea.

The reduced diameter of the contact lens 40 eliminates the scleral portion of the conventional diagnostic or therapeutic contact lens, such that when the posterior surface 44 is applied to cornea 12, the extent of the lens will not reach beyond the limbal region 14 or onto the sclera 16 of eye 10. By reducing the diameter of the contacting posterior surface to an effective diameter of less than or equal to 10.0 mm in conjunction with the preferred aspheric curve described above, air trapped between the lens and the cornea upon application to the cornea, will be displaced. The diagnostic or therapeutic contact lens 40 may be positioned within a housing 48 of any desired configuration, and may include threads to allow the contact lens 40 to be screwed into housing 48 in a convenient manner.

Turning now to FIGS. 3–6, an alternate and preferred embodiment of the contact lens is shown generally at 60. The diagnostic or therapeutic contact lens 60 includes an anterior surface 62 which may be of any configuration as previously described, but is shown to have a convex surface. The lens 60 also includes a concave posterior surface 64 positioned on cornea 12. In this embodiment, the posterior surface 64 includes a scleral portion 66, which extends beyond the limbal region and onto the sclera of eye 10. The scleral portion 66 facilitates positioning of the diagnostic or therapeutic contact lens 60 on the cornea 12, and helps to maintain or stabilize this position. The eyelids of the patient may extend over the scleral portion 66 during diagnosis or treatment with lens 60.

Figure 5:
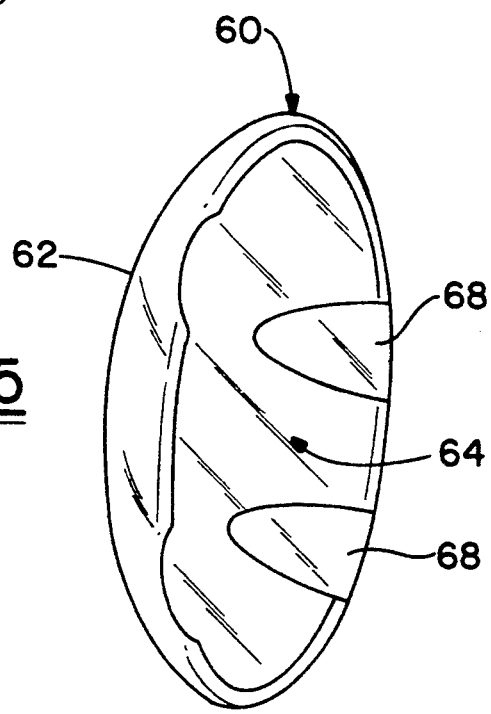
FIG. 5 is a perspective view of the diagnostic or therapeutic contact lens as shown in FIG. 3.
Figure 6:
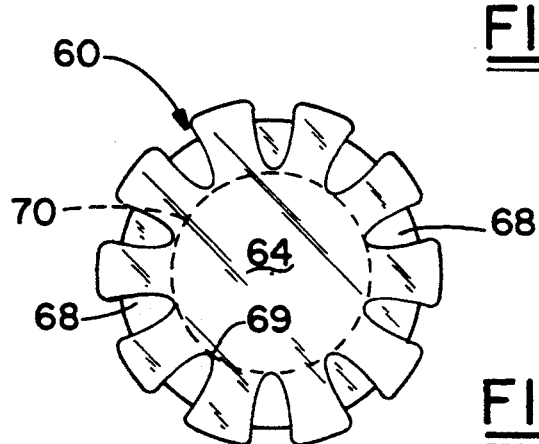
FIG. 6 is a plan view of the posterior surface of an alternate embodiment of the contact lens as shown in FIG. 3.

In this embodiment of the invention, the diagnostic or therapeutic contact lens 60 includes a plurality of channels 68 extending from a center optical region 70 to the periphery of posterior surface 64. The channels 68 may extend to the peripheral edge of the posterior surface 64 so as to create a vent to the exterior of the contact lens 60. As seen in FIG. 5, The channels 68 may extend to the peripheral edge of the surface 64 without intersecting the anterior surface 62, or the depth of the channels 68 may be such that the channels will intersect the anterior surface 62 as seen in FIG. 6.

The channels 68 formed in the posterior surface 64 of the diagnostic or therapeutic contact lens 60 provide the means for permitting the egress of air from the precorneal region about the optically functional region 70 of the posterior surface 64. The channels 68 will facilitate the displacement of air from between the cornea 12 and contact lens 60 in the region of optical portion 70 to the exterior of lens 60 or at least away from region 70 so as not to inhibit optical performance of the diagnostic or therapeutic lens.

In any particular diagnostic or therapeutic procedure, a portion of the contact lens 60 will be utilized to transmit light rays through the contact lens 60 and into the patient's eye 10 and/or transmit light rays exiting from the patient's eye 10 to form an image of the desired portion of the eye being examined. Thus, for any particular diagnostic or therapeutic procedure, the channels 68 will not extend into the optically functional portion 70, precluding possible aberration or distortion of light rays due to the channels 68. In many instances, the center region of the posterior surface 64 will be the area of the lens adapted to transmit light rays, and the channels 68 will therefore extend from this center region radially to the periphery of the posterior surface 64. Alternatively, the channels 68 may be formed to extend radially or otherwise from any portion of the lens through which light rays are to be transmitted for illumination, image formation, laser treatment or the like.

Figure 4:
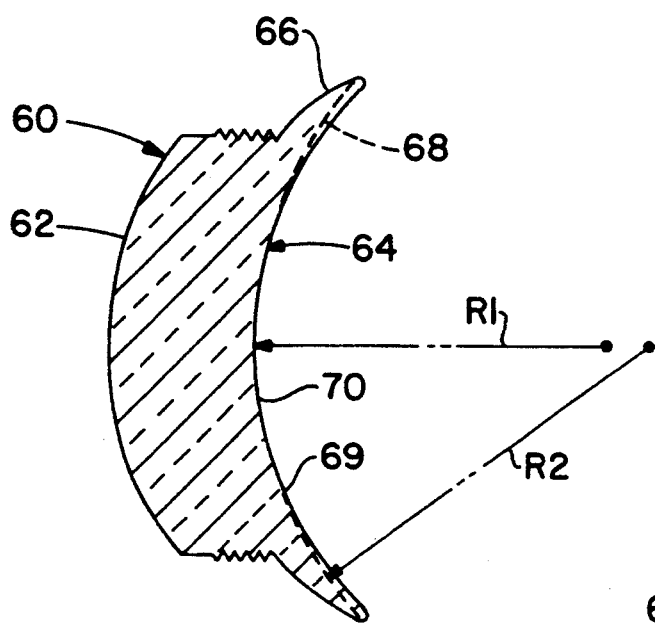
FIG. 4 is an enlarged vertical cross-sectional view of the embodiment of the contact lens as shown in FIG. 3.
Figure 7A:
FIGS. 7a and 7b show enlarged cross-sections of alternate profiles of the channels to permit the egress of air from the precorneal space, associated with the preferred embodiment of the diagnostic or therapeutic contact lens of the invention.

Turning to FIG. 7a, the cross-sectional profile 80 of a first embodiment of channels 68 is shown. In forming channels 68, they will have a predetermined cross-sectional profile, which may be modelled as a portion of a concave barrel torus as shown at 82. In the manufacture of the contact lens 60, the channels 68 may be formed by cutting or abrading of the lens material along a surface profile intersecting the posterior surface 64. As seen in FIG. 4, the posterior surface 64 may have an apical radius of curvature, $R_1$, while the surface profile of the channels has an apical radius of curvature, $R_2$, which is slightly flatter than $R_1$ so as to intersect the posterior surface 64. This surface profile is modelled as a concave barrel torus which can be described by two principal meridians along any point of the toric curve. In the preferred embodiment, the posterior surface 64 will have an apical radius of curvature of between 7.6 mm and 7.8 mm, and may be of aspheric contour having an apical eccentricity of approximately 0.6. The intersecting surface profile of the formed channel 68 for a posterior surface 64 of the above-described configuration, may have an equatorial radius, extending along the channel, ranging from the apical radius of the posterior surface 64 to a flat surface, with a radius of approximately 9.7 mm being preferred. The transequatorial radius of the channel, seen in the cross-section of FIG. 7a, may range from 0.3 to 5.0 mm with a radius of approximately 1.2 mm being preferred. In the preferred embodiment, the equatorial radius of the formed channel 68 provides a surface contour which approximates the aspheric posterior surface of the lens, but which is slightly flatter than the shape of the posterior surface. The channel 68 will therefore have increasing depth from its point of intersection with the posterior surface to the peripheral edge of the lens.

Figure 7B:

Alternatively, as seen in FIG. 7b, the channels 68 may be formed as having an apheric profile 85, wherein the channels will be modeled as a portion of a sine curve. In this configuration, the deepest point 86 of the channels will correspond to the trough portion of a sine wave at which the slope of the curve becomes zero. The intersection of the channel with the posterior surface 64 shown at 88, at some point along the traverse of the channel from its point of intersection 69 with surface 64, to the most peripheral edge of the channel, coincides with the peaks of the sine curve, wherein again the slope of the curve becomes zero. The channel is tangent to the posterior surface 64 at the respective peaks of the sine curve coinciding with the points of intersection 88 with surface 64. The channels 68 are therefore modelled as the portion of the sine curve from $\pi/2$ to $5\pi/2$, with the peaks at $\pi/2$ and $5\pi/2$, and the trough or deepest point 86 of the channels 68 corresponding to $3\pi/2$ of the sine curve. Another suitable channel cross-sectional profile to accomplish the aspects of the invention is a portion of a conic section, which may be both deeper and flatter along its peripheral portion relative to a channel with a circular profile, so as to reduce the acuteness of the juncture of the channel to the posterior surface 64.

In the preferred embodiment, the increased depth of the formed channel 68 provides an increased volume from the position adjacent the center or optical portion 70 of the posterior surface 64 toward the periphery of the lens. The increased volume of channels 68 allows air to be displaced into the channels and facilitate the egress of air from the precorneal region. As an alternative to an increasing depth, or in conjunction therewith, the width of the channels may also be varied. As seen in FIG. 4, the depth and/or width of channels 68 may be varied from the point of intersection with the posterior surface 64 at 69, with a very shallow depth and/or width, to a maximum depth and/or width at a peripheral region of the channel 68. The channel 68 may be tapered continuously and progressively from the optical portion of the posterior surface 64 such that the channel will intersect the anterior surface 62 at its maximum depth and allow the egress of air from the channel. Further, the channel 68 allows the infusion of air and tear fluid back to the precorneal space when the lens is removed so as to minimize suction between the lens and cornea.

The thickness of the diagnostic or therapeutic contact lens 60 enables formation of channels of the desired depth. As a diagnostic or therapeutic contact lens is designed to maintain the eyelids of the patient open, the thickness of the lens is significantly greater than conventionally utilized with vision-correcting prescription contact lenses. The depth of the channel 68 may vary from point 69, where it first intersects surface 64, to a depth of 0.2 mm or more along its length. The depth of the channel, normal to the posterior surface, at the peripheral edge of the lens is about 0.5 mm in the preferred embodiment. The width of the channels 68 may also be varied from a location adjacent the optically functional region of the posterior surface 64 either alone or in conjunction with variation of depth of the channels 68. A milling procedure to form channels 68 in the posterior surface 64 can be used to increase the width of the channel 68 in a continuous and progressive manner to the peripheral edge of the lens. Alternatively, the channel 68 may be of a maximum depth and/or width at a point along the length of the channel, and thereafter be shallower or narrower toward the peripheral edge of the lens. It should be recognized that increasing the depth and/or width of the channel 68 on the posterior surface 64 will provide an increased volume toward the peripheral edge of the lens and away from the optically functional portion of the posterior surface. It should also be recognized that other configurations for the channels may be used to facilitate the egress of air from the precorneal space, which may be particularized to the diagnostic or therapeutic procedure and lens type being used.

Another embodiment of the invention is shown in FIGS. 8 and 9 wherein the posterior surface 92 of a diagnostic or therapeutic contact lens 90 includes means to permit the egress of air from the precorneal region, which comprise channels 94 formed in posterior surface 92. The channels 94 of this embodiment extend across the entire posterior surface 92 of the diagnostic or therapeutic contact lens body. The channels 94 therefore extend through the optically functional region of the contact lens 90, which is adapted to transmit light rays entering or exiting from the eye. In this embodiment, the presence of the channels 94 in the optically functional region of the posterior surface 92 would conventionally cause unwanted aberrations or distortions due to the disconformity of the surface. To overcome this problem, the diagnostic or therapeutic contact lens of this embodiment is preferably fabricated from a transparent, dimensionally stable solid material characterized by an index of refraction approximating that of natural human tears. In this manner, the indices of refraction on either side of the interface between the contact lens 90 and the cornea of the eye will not result in a refractive or vergence power change at the interface due to varying indices of refraction. The index of refraction of human tears is approximately 1.336, and materials have been developed which are characterized by an index of refraction approximating this value. For example, copolymers and terpolymers of perfluoro-2-methylene-4-methyl-1,3-dioxolane, referred to as PMD, or copolymers of tetrafluoroethylene have been found to have a refractive index of the desired value, and exhibit good clarity and hardness properties. A description of suitable materials for the fabrication of the diagnostic or therapeutic contact lens in accordance with this embodiment are described in U.S. Pat. No. 3,542,461, which is hereby incorporated by reference and made a part hereof.

By fabricating the contact lens 90 of a material characterized by an index of refraction approximating that of human tears, the variance of index of refraction at the interface between the channels 94 and the cornea of the eye will be eliminated as long as the natural tear layer formed on the eye fills the space in the optical region of lens 90 at the location of channels 94. The channels 94 may therefore be configured to have a minimum width and/or depth in the optical region of the lens, to facilitate filling of the region with tear fluid produced by the eye. From the optical region of the lens, the channels 94 may thereafter have increasing depth and/or width as previously described, to increase the volume within the channel and facilitate the egress of any trapped air from the precorneal space and the optical region of the lens to the exterior or peripheral portions of the lens. Thus, in the embodiment as shown in FIGS. 8 and 9, with the center portion of the lens being the optically functional portion, the channels 94 will be narrow and/or shallow within the center region and will be of increasing width and/or depth in directions radially extending from the center optical portion.

Another embodiment of the invention is shown in FIGS. 10 and 11, wherein a contact lens 95 having a posterior surface 96 is shown. In this embodiment, the anterior surface is shown to be a planar surface, and the means to permit egress of air comprise either/or a series of channels 97 or a plurality of apertures or holes 98 formed in surface 96. The channels 97 additionally may include apertures or holes 99, formed in a peripheral region of the channels 97. The holes 98 or 99 communicate with an exterior portion of the lens 80 to permit the egress of air from the precorneal region or channels 84 respectively. The holes 98 may be positioned in the area adjacent the optically functional portion of the lens to permit the egress of air and allow immediate displacement of air from between the cornea and contact lens about the optically functional portion thereof. The holes may be of very small diameter while still allowing the egress of air therethrough. Although the channels 97 are not shown to extend to the periphery of the lens and through a scleral portion thereof, it should be recognized that other configurations are contemplated as described with reference to other embodiments of the invention.

Turning now to FIG. 12, there is shown another alternative embodiment of the present invention, wherein the posterior surface 102 of a contact lens 100 is formed as having means for the egress of air from the precorneal space between the posterior surface 102 and the cornea of an eye on which the lens is positioned. In this embodiment, the optically functional region of the posterior surface 102, depicted at 104, is surrounded by an inscribed channel 106 which circumferentially extends about region 104. The inscribed channel 106 may be formed to have a relatively shallow depth and/or width, and functions to allow displacement of air therein from the precorneal region between the posterior surface 102 and the cornea of the eye. Also in this embodiment, a plurality of channels 108, which extend radially from the optically functional region 104, are adapted to communicate with channel 106 to allow the egress of displaced air from the precorneal region. The channels 108 may be configured in a manner similar to that described with respect to previous embodiments, to have an increasing width and/or depth toward the peripheral edge of surface 102. Additionally, the plurality of channels 108 may terminate before the peripheral edge of the lens, while still accommodating displaced air from the precorneal region, or may be connected to a hole connected to the exterior of the lens as in previous embodiments.

Figure 14:
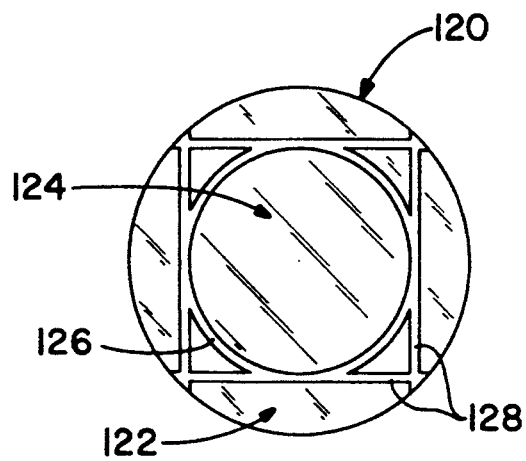
FIG. 14 shows a plan view of the posterior surface of an alternate embodiment of the diagnostic or therapeutic contact lens of the invention.
Figure 15:
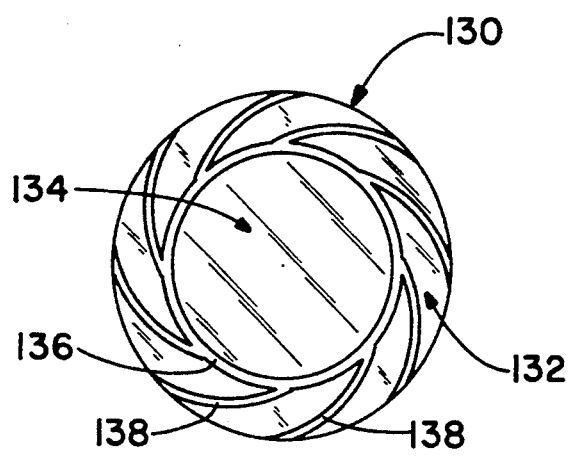
FIG. 15 shows a plan view of the posterior surface of a another alternate embodiment of the diagnostic or therapeutic contact lens of the invention.

A variety of other configurations for the means to permit egress of air from the precorneal region upon application of the contact lens to the eye are shown in FIGS. 13–17. In FIG. 13, a contact lens 110 has a posterior surface 112 with a plurality of channels formed therein to permit the egress of displaced air from the precorneal region. An optically functional region 114 of the posterior surface 112 may include a channel 116 which is inscribed circumferentially about the optically functional region 114. Communicating with channel 116 may be a plurality of channels 118, formed as semicircles which extend from the peripheral edge of the posterior surface 112 and inwardly to intersect with the circumferentially inscribed channel 116. The plurality of channels 118 allows the egress of displaced air which has been drawn into channel 116 in the desired manner. Similarly, as seen in FIG. 14, a diagnostic or therapeutic lens 120 having a posterior surface 122 includes an optically functional region 124. The optically functional region 124 is surrounded by a circumferentially inscribed channel 126, which in turn communicates with a plurality of channels 128 extending from the peripheral edge of posterior surface 122. The channels 128 are positioned to extend approximately tangent to the circumferentially inscribed channel 126, but will intersect channel 126 to allow the egress of air from channel 126 to the exterior of the lens via channels 128. It should be recognized that although channels 128 have been shown to be symmetrical in FIG. 13, other configurations in which channels 128 are formed tangential and intersecting with channel 126 are contemplated. In FIG. 15, a diagnostic or therapeutic contact lens 130 having a posterior surface 132 includes an optically functional region 134. The optically functional region 134 is surrounded by a circumferentially extending channel 136, which in turn communicates with a plurality of channels 138 which extend to the peripheral edge of the lens 130. The channels 138 extend spirally from the peripheral edge of the posterior surface 132 so as to intersect the circumferentially inscribed channel 136 at a point of tangency between channel 136 and the arc of channels 138. In the embodiments as shown in FIGS. 11–14, air displaced from the precorneal region in the optically functional region of the diagnostic therapeutic lens will be displaced to a circumferentially inscribed channel which communicates with additional channel means extending to the peripheral edge of the lens to allow the egress of air in the desired manner. Additionally, the channels extending to the peripheral edge of the contact lens, or communicating with a through-hole or the like as described in previous embodiments, result in minimizing any suction between the posterior surface of the contact lens and the cornea of the eye upon removal of the lens from the eye.

Figure 16:
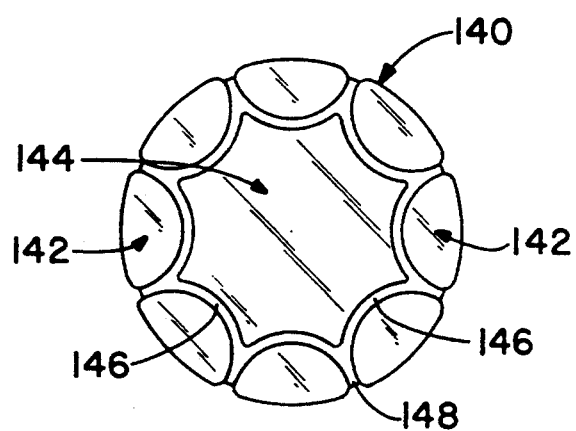
FIG. 16 shows a plan view of the posterior surface of a another alternate embodiment of the diagnostic or therapeutic contact lens of the invention.
Figure 17:
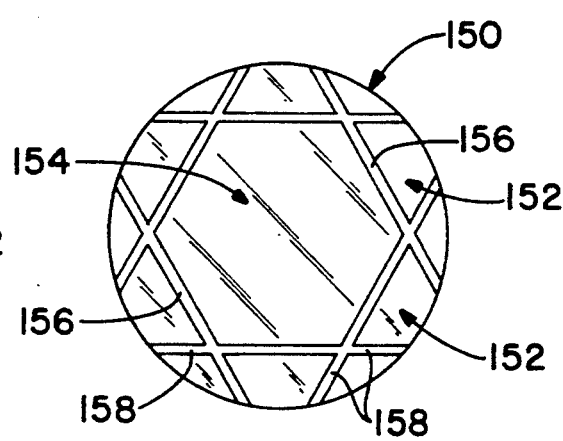
FIG. 17 shows a plan view of the posterior surface of a another alternate embodiment of the diagnostic or therapeutic contact lens of the invention.

Turning to FIGS. 15 and 16, several other alternate embodiments are shown which include alternative means to permit the egress of air from the precorneal space. In FIG. 16, a contact lens 140 having a posterior surface 142 includes an optically functional region 144. Surrounding the optically functional region 144 is a plurality of channels 146, which together surround the optically functional region 144 at a number of distinct locations. The channels 146 may be formed as having semicircular configurations, and extend from the peripheral edge of the posterior surface 142 toward the optically functional region 144. Upon application of the contact lens 140 to the cornea of the eye, air trapped in the precorneal region will be displaced from the optically functional region 144 and will be drawn into the channels 146 surrounding region 144. The channels 146 will facilitate the egress of air from the precorneal space in the desired manner. An alternate embodiment is shown in FIG. 17, wherein the contact lens 150, including a posterior surface 152 is provided with a plurality of channels 156 which extend about an optically functional region 154. The channels 156 permit the egress of displaced air from the optically functional region 154 to the exterior of the contact lens 150 as desired. In the embodiments of FIG. 16 and 17, the means to permit the egress of air comprise channels which extend in a substantially tangential position relative to the optically functional region of the posterior surface of the lens. A plurality of channels are provided in order to substantially surround the optically functional region of the posterior surface and allow the displacement of air from the precorneal space into a respective channel in the desired manner.

While the invention has been described and illustrated with reference to various specific embodiments, it is to be understood that various modifications of the invention are contemplated and would occur to those skilled in the art, and are encompassed within the invention without departing from the spirit of the invention or the scope of the appended claims.

What is claimed:

1. A diagnostic or therapeutic contact lens for use in examination or treatment of the eye of a patient comprising,
   a lens body constructed of a rigid, transparent material and having a concave posterior surface with a curvature substantially conforming to the curvature of the cornea of the eye, said posterior surface being movable on said cornea during examination or treatment of the eye, a peripheral edge formed by the thickness of said lens body wherein the thickness of said lens body will prevent closure of the eyelid of said eye when the contact lens is positioned in the cornea of the eye, and an anterior surface spaced from posterior surface by the thickness of said lens body,
   said posterior surface having means for permitting the egress of air from between said posterior surface and the surface of the cornea to substantially eliminate the formation of air bubbles in at least the optical portion of said posterior surface which would adversely affect examination or treatment of the eye using the contact lens.

2. The diagnostic or therapeutic contact lens as in claim 1, wherein,
   said means for permitting the egress of air comprises at least one channel formed in said posterior surface, said at least one channel being positioned relative to said optical region, such that air entrapped between said posterior surface and the cornea will be displaced from said optical region into said at least one channel.

3. The diagnostic or therapeutic contact lens of claim 2, wherein,
   said at least one channel extends from said optical portion of the posterior surface toward the peripheral edge and communicates with the peripheral edge of said lens body.

4. The diagnostic or therapeutic contact lens of claim 2, wherein,
   a plurality of channels are formed in said posterior surface, with at least one of said plurality of channels being inscribed in said posterior surface about said optical portion, and at least one other of said plurality of channels extends from said inscribed channel toward and communicates with the peripheral edge of said lens body.

5. The diagnostic or therapeutic contact lens of claim 2, wherein,
   said at least one channel extends radially from said optical portion of the posterior surface toward the peripheral edge of said lens, but terminates prior to the peripheral edge of said lens body, and said means to permit egress of air further comprises at least one hole communicating with said at least one channel and the exterior.

6. The diagnostic or therapeutic contact lens of claim 2, wherein,
   said at least one channel is formed as a portion of a concave barrel torus having a curvature which is flatter than the curvature of said posterior surface such that said at least one channel will have increasing depth from its point of intersection with said posterior surface to the peripheral edge of said lens body.

7. The diagnostic or therapeutic contact lens of claim 2, wherein,
   said at least one channel is formed as a portion of a sine curve from $\pi/2$ to $5\pi/2$, with the peaks at $7\pi/2$ and $5\pi/2$ intersecting said posterior surface and the point of said at least one channel corresponding to $3\pi/2$ of said portion of said sine curve forming the deepest part of said at least one channel.

8. The diagnostic or therapeutic contact lens of claim 2, wherein,
   said at least one channel has an increasing volume away from said optical portion of said posterior surface such that air bubbles trapped between said posterior surface and said cornea will be displaced into said at least one channel and away from said optical portion of said contact lens upon placement of said contact lens on said cornea.

9. The diagnostic or therapeutic contact lens of claim 8, wherein,
said at least one channel varies in width along its extent, resulting in said increasing volume in the direction away from said optical portion of said posterior surface.

10. The diagnostic or therapeutic contact lens of claim 8, wherein,
said at least one channel has a varying depth along its extent, resulting in said increasing volume in the direction away from said optical portion of said posterior surface.

11. The diagnostic or therapeutic contact lens of claim 8, wherein,
said at least one channel has a varying depth and varying width along its extent, resulting in said increasing volume in the direction away from said optical portion of said posterior surface.

12. The diagnostic or therapeutic contact lens of claim 1, wherein,
said means for permitting the egress of air comprises at least one channel formed in said posterior surface and passing through said optical portion of said posterior surface, said at least one channel having a minimum volume in said optical portion so as to facilitate filling of said at least one channel with a tear fluid in said optical portion.

13. The diagnostic or therapeutic contact lens of claim 12, wherein,
said material from which said lens body is made has an index of refraction approximating the index of refraction of natural human tears.

14. The diagnostic or therapeutic contact lens of claim 12, wherein,
said at least one channel extends from said optical portion of the posterior surface toward and communicates with the peripheral edge of said lens body.

15. The diagnostic or therapeutic contact lens of claim 12, wherein,
said at least one channel varies in width along its extent, and has an increasing volume in the direction away from said optical portion of said posterior surface.

16. The diagnostic or therapeutic contact lens of claim 12, wherein,
said at least one channel has a varying depth along its extent, and an increasing volume in the direction away from said optical portion of said posterior surface.

17. The diagnostic or therapeutic contact lens of claim 12, wherein,
said at least one channel has a varying depth and varying width along its extent, and an increasing volume in the direction away from said optical portion of said posterior surface.

18. The diagnostic or therapeutic contact lens of claim 1, wherein,
said means for permitting the egress of air comprises a plurality of apertures communicating with said posterior surface and the exterior atmosphere, said plurality of apertures being positioned outside of and adjacent to said optical portion of said posterior surface.

19. A diagnostic or therapeutic contact lens for use in examination or treatment of the eye of a patient, comprising,
a lens body constructed of a rigid, transparent material and having a thickness, said lens body including a concave posterior surface having a curvature substantially conforming to the curvature of the cornea of an average human eye and adapted to be selectively positioned on the cornea during examination or treatment of the eye, and an anterior surface being spaced from said posterior surface by the thickness of said lens body such that said anterior surface is positioned outside of the lid of the eye, wherein said thickness of said lens body will prevent closure of the lid when the contact lens is positioned on said cornea,
said posterior surface having a diameter which is smaller than the cornea of an average human eye such that said posterior surface may be positioned on the cornea without contacting the limbal area or scleral portion of the average human eye, wherein said posterior surface may be positioned and translationally moved on the cornea while minimizing suction between the posterior surface of the lens body and said cornea, and eliminating the use of an ophthalmic solution in association with the diagnostic or therapeutic contact lens in the examination or treatment procedure.

20. A diagnostic or therapeutic contact lens for use in examination or treatment of the eye of a patient, comprising,
a lens body constructed of a rigid, transparent material and having a thickness, said lens body having a concave posterior surface with a curvature substantially conforming to the curvature of the cornea of said eye and adapted to be selectively positioned on said cornea during examination or treatment of the eye, and an anterior surface being spaced from said posterior surface by the thickness of said lens body, such that said anterior surface is positioned outside of the lid of the eye, wherein said thickness of said lens body will prevent closure of the eyelid when the contact lens is positioned on the cornea,
said posterior surface including means associated with said posterior surface for permitting the egress of air from the region between the corneal surface and said posterior surface so as to allow tear fluid of said eye to interface between said posterior surface and the corneal surface in said optical region, wherein light transmission through said optical region will not be adversely affected by entrapped air between said lens body and said corneal surface.

* * * * *